United States Patent
Francavilla (10) Patent No.: US 8,932,265 B2
(45) Date of Patent: Jan. 13, 2015

(54) HOLDER WITH SAFETY SHIELD FOR A DRUG DELIVERY DEVICE

(75) Inventor: Frank Francavilla, Newton, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 2769 days.

(21) Appl. No.: 10/543,878

(22) PCT Filed: Jan. 30, 2004

(86) PCT No.: PCT/US2004/002786
§ 371 (c)(1),
(2), (4) Date: Jul. 28, 2005

(87) PCT Pub. No.: WO2004/069302
PCT Pub. Date: Aug. 19, 2004

(65) Prior Publication Data
US 2006/0276756 A1    Dec. 7, 2006

Related U.S. Application Data

(60) Provisional application No. 60/443,826, filed on Jan. 30, 2003.

(51) Int. Cl.
*A61M 5/32* (2006.01)
*A61M 5/31* (2006.01)
*A61M 5/46* (2006.01)
*A61M 5/42* (2006.01)

(52) U.S. Cl.
CPC ........... *A61M 5/3129* (2013.01); *A61M 5/3257* (2013.01); *A61M 5/326* (2013.01); *A61M 5/46* (2013.01); *A61M 5/3243* (2013.01); *A61M 5/425* (2013.01); *A61M 2205/583* (2013.01); *A61M 2205/6063* (2013.01)

USPC .......................................... 604/197; 604/198

(58) Field of Classification Search
CPC ........... A61M 5/3129; A61M 5/3243; A61M 5/3257; A61M 5/3271
USPC ......................................... 604/110, 192–198
See application file for complete search history.

(56) References Cited

U.S. PATENT DOCUMENTS

| 3,880,163 A | 4/1975 | Ritterskamp |
| 4,601,708 A | 7/1986 | Jordan |
| 4,787,891 A | 11/1988 | Levin et al. |

(Continued)

FOREIGN PATENT DOCUMENTS

| FR | 2654346 A1 | 5/1991 |
| FR | 2799975 A1 | 4/2001 |

(Continued)

*Primary Examiner* — Matthew F Desanto
(74) *Attorney, Agent, or Firm* — Hoffmann & Baron, LLP (57) ABSTRACT

A holder with a safety shield for a drug delivery device; the shield obstructing access to a needle of the drug delivery device following use thereof. The safety shield may be actively deployed, in which case the health care worker must perform an action beyond complete depression of the pusher into the body of the drug delivery device to deploy the shield. Alternatively, the safety shield may be deployed passively or automatically, in which case deployment of the shield occurs upon complete depression of the pusher into the body, with no additional action required of the health care worker. The safety shield is spring-loaded and released to its extended position by a mechanical coupling of a series of position members, including levers, formed on the holder and the drug delivery device.

16 Claims, 8 Drawing Sheets

(56) References Cited

U.S. PATENT DOCUMENTS

| | | | |
|---|---|---|---|
| 5,141,496 A * | 8/1992 | Dalto et al. | 604/117 |
| 6,371,938 B1 | 4/2002 | Reilly et al. | |
| 6,494,865 B1 | 12/2002 | Alchas | |
| 6,776,777 B2 * | 8/2004 | Barrelle | 604/198 |
| 6,846,302 B2 * | 1/2005 | Shemesh et al. | 604/110 |

FOREIGN PATENT DOCUMENTS

| | | |
|---|---|---|
| WO | 9426335 A1 | 11/1994 |
| WO | 0141841 A2 | 6/2001 |
| WO | 03000323 A1 | 1/2003 |
| WO | 03068298 A1 | 8/2003 |

* cited by examiner

HOLDER WITH SAFETY SHIELD FOR A DRUG DELIVERY DEVICE

This application claims priority of U.S. Provisional Appl. No. 60/443,826, filed Jan. 30, 2003.

BACKGROUND OF THE INVENTION

The present invention relates to an injection device comprising a holder with a safety shield for a drug delivery device and more particularly, to a holder having a deployable safety shield that may be deployed to cover the end of a needle cannula after use to prevent exposure of the user to the contaminated needle and to reduce the risk of injury from accidental needle-stick.

The risks of accidental needle-stick injury following use of a drug delivery device, such as a hypodermic syringe, are well known. In fact, legislation has been enacted in the United States requiring that certain types of syringes include features intended to reduce or eliminate the possibility of accidental needle-stick. In addition to any Federally mandated requirements for such features, any device for use in connection with a syringe intended to address the risk of needle-stick injury should be simple to use and reliable so as to ensure that the device performs its intended function in every instance.

Many devices have been developed for shielding needles after use. Some of these devices are complex, and some require considerable manipulation by the user to position the shield about the needle to protect the user. In some cases, such manipulation may require the use of both hands of the user.

Some prior art devices having deployable shields for shielding needles may lack precise control for deploying the shield. As a result, the shield may deploy when such deployment is not intended. Such unintended deployment may have numerous disadvantages. For example, if the deployment occurs when the needle is inserted into the patient, then this may interfere with the dispensing of the medication contained in the syringe. In some prior art devices, unintended deployment may also occur during shipment of the device (assembled with or without a syringe) rendering the device unusable for an actual injection.

SUMMARY OF THE INVENTION

The present invention is directed to a holder for a drug delivery device such as, for example, a hypodermic syringe assembly. The inventive holder includes a selectively deployable safety shield that prevents access to the needle forward tip following use of the syringe assembly to enhance safety of the user. The present invention is also directed to an injection device comprising a drug delivery device contained within a holder having a selectively deployable safety shield that prevents access to the contaminated needle forward tip after use of the drug delivery device.

The inventive holder includes a deployable safety shield that extends to cover the forward tip of the needle following injection by the health care worker. In one aspect of the subject invention, the safety shield may be "actively" deployed by performance of an action beyond the normal completion of the injection stroke of the pusher in the syringe body. In a further aspect of the subject invention, the safety shield may be "passively" deployed upon completion of the injection stroke with no additional action required of the health care worker.

The safety shield of the holder is spring-loaded and movable from a first or retracted position in which the forward tip of the needle is exposed, to a second or extended position in which the forward tip of the needle is contained within the safety shield. The safety shield is biased by a biasing means to move from the first position to the second position. The safety shield may be released from the first position by alignment and mechanical coupling of a plurality of components, including components provided on the holder and syringe. Prior to use of the drug delivery device, those plurality of components are not all in alignment and activation of the safety shield is not possible, i.e., the safety shield cannot be caused to move from the first position to the second position under bias by the spring. Once the complete dose of medicament contained in the medical device is injected into the patient, the plurality of components are brought into alignment and may be mechanically coupled together to effect release of the safety shield from the first position and enable movement of the safety shield from the first position to the second position.

These and other features of the invention will be more fully understood from the following description of specific embodiments of the invention taken together with the accompanying drawings.

BRIEF DESCRIPTION OF THE DRAWINGS

In the drawings, wherein like reference characters denote similar elements throughout the several views.

DETAILED DESCRIPTION OF THE INVENTION

The present invention is directed to a holder and to an injection device having the combination of the holder and drug delivery device. The holder includes a housing and a safety shield provided in the housing movable from a first or retracted position, in which a forward tip of a needle cannula of the drug delivery device is exposed, to a second or extended position, in which the forward tip of the needle cannula is contained within the safety shield. The drug delivery device is preferably a syringe comprising a body having proximal and distal ports and a reservoir within which a drug substance may be held. The syringe further comprises a needle cannula provided on the body, the needle cannula having a forward tip, preferably sharpened, and a rearward tip in fluid communication with the reservoir. The syringe further comprises a pusher including a pusher cap having a cap wall, a pusher stem and a stopper at one end of the pusher stem. The stopper is movable in the reservoir in a proximal to distal direction over a length defining an injection stroke. Various components provided on the housing and drug delivery device are selectively alignable when the stopper has been caused to be inserted into the reservoir a predetermined extent, i.e., upon completion of an injection stroke. Alignment of the various components enables the safety shield to be released from its first or retracted position. Release of the safety shield upon alignment of the various components may be effected by the user depressing or activating a release mechanism, or it may occur automatically upon completion of the injection stroke. Once activated, the safety shield is caused to move by a biasing means such as, for example, a coil spring, from the first position to the second or extended position.

The terms "distal" and "proximal" are used herein as reference designations only to facilitate description of the present invention. As used herein, the term "distal" refers to a location, element or component that is near the patient (i.e., the needle end of the device), and the term "proximal" refers to a location, element or component that is near the user of the injection device (i.e., the pusher cap end of the device).

Referring next to the drawings, the various embodiments of the present invention will now be discussed in detail. Referring first to FIGS. 1 to 6, an injection device is depicted and generally identified by reference character 10. The inventive injection device 10 comprises a holder 200 and a drug delivery device. By way of non-limiting example, the drug delivery device is shown to be a syringe and is designated by the reference numeral 18. Other drug delivery devices may be used with the subject invention and any syringe design may be used. For illustrative purposes, a particular syringe design is described and depicted herein. The syringe 18, as shown in FIGS. 2 and 4-6, includes a longitudinally elongate syringe body 11 having an internal reservoir 12 for containing a drug substance, that term being used herein to refer to any liquid medicament injectable into a patient, including, by way of illustration and not limitation, therapeutic drugs, vaccines, and the like. The syringe body 11 has a distal port 13 through which the drug substance contained in the reservoir may exit therefrom. The syringe body 11 also has a proximal port 14. A needle cannula 16 is in fluid communication with the reservoir 12 via the distal port 13. The holder 200 provides shielding of the needle cannula 16 after use of the injection device 10 to reduce the likelihood of accidental needle-stick injury to the user or patients.

The syringe 18 further has a pusher 250 which includes a cylindrical pusher cap 252 having a longitudinal cavity 254 which is bounded by a cap wall 256. The pusher 250 further includes a pusher stem 258 connected in coaxial relation to the cap 252 for insertion of the pusher stem through the proximal port 14 into the reservoir 12. The distal end of the pusher stem 258 is constituted by a plunger or stopper 24. With the pusher stem 258 acting on the plunger 24, the proximal to distal advancement of the pusher stem 258 into the reservoir 12 reduces the volume thereof resulting in the exiting of the drug substance through the distal port 13.

Figure 4:
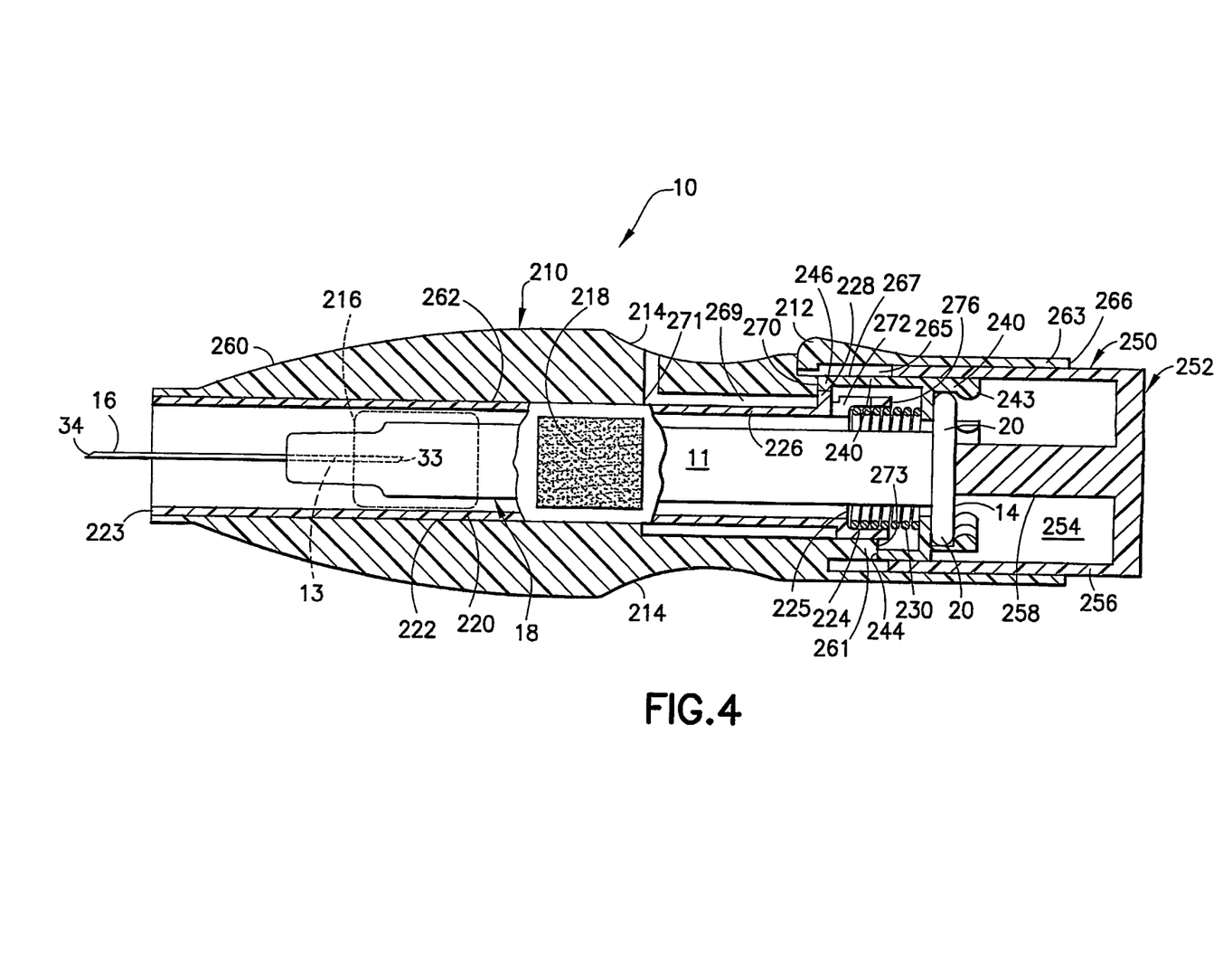
FIG. 4 is a cross-sectional side view of the holder and drug delivery device of FIG. 1 prior to use.

The needle cannula 16 has rearward and forward tips 33, 34, respectively (FIG. 4). The needle cannula 16 is supported on the syringe body 11 such that the forward tip 34 is distal of the syringe body 11. The rearward tip 33 of the needle cannula 16 is in fluid communication with the reservoir 12 through the distal port 13 such that drug substance within the reservoir can flow through the needle cannula 16 and exit through the forward tip 34. The needle cannula 16 may have any length, depending upon the type of injection desired. For example, the inventive injection device 10 may be used to deliver intramuscular, subcutaneous, intradermal, interstitial, or other types of injections. In an alternative embodiment (see, e.g., FIGS. 5 and 6), a limiter 300 may be provided on the distal end of the syringe body 18 such as that disclosed in U.S. Pat. No. 6,494,865 B1, the entire disclosure of which is hereby incorporated by reference herein. The limiter 300 defines a skin engaging surface 310 having a preferred outer diameter of approximately 5.5 mm. The forward tip 34 of the needle cannula 16 extends beyond the skin engaging surface 310 a distance ranging from 0.5 mm to 3 mm. The combination of the skin engaging surface 310 and limited length of the needle cannula 16 provide a device particularly well-suited for administering an injection into the intradermal space of a patient's skin. As will be appreciated by those skilled in the art, any skin engaging surface configuration may be used with the subject invention to achieve intradermal injections.

Figure 1:
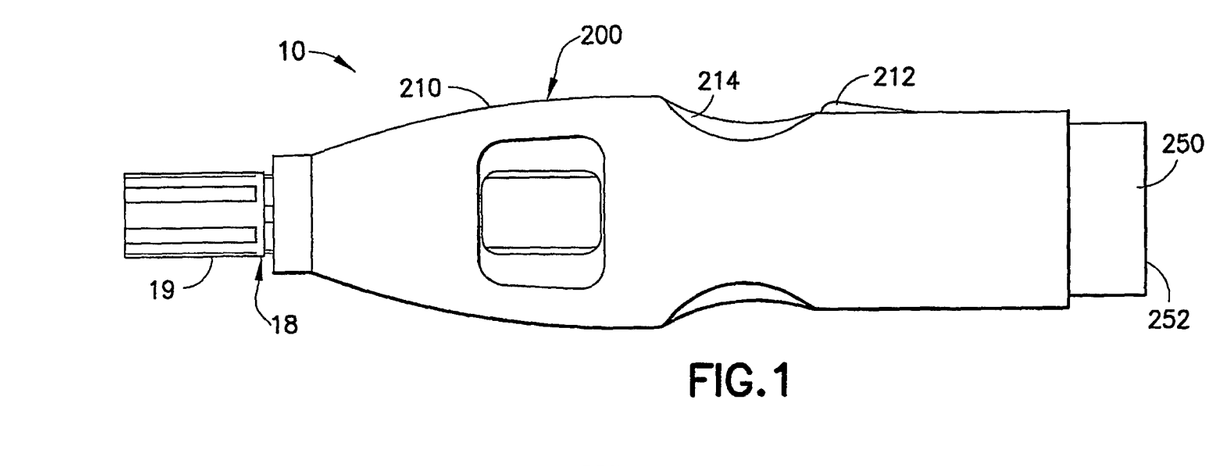
FIG. 1 is a side view of a drug delivery device and holder constructed in accordance with an embodiment of the present invention.
Figure 2:
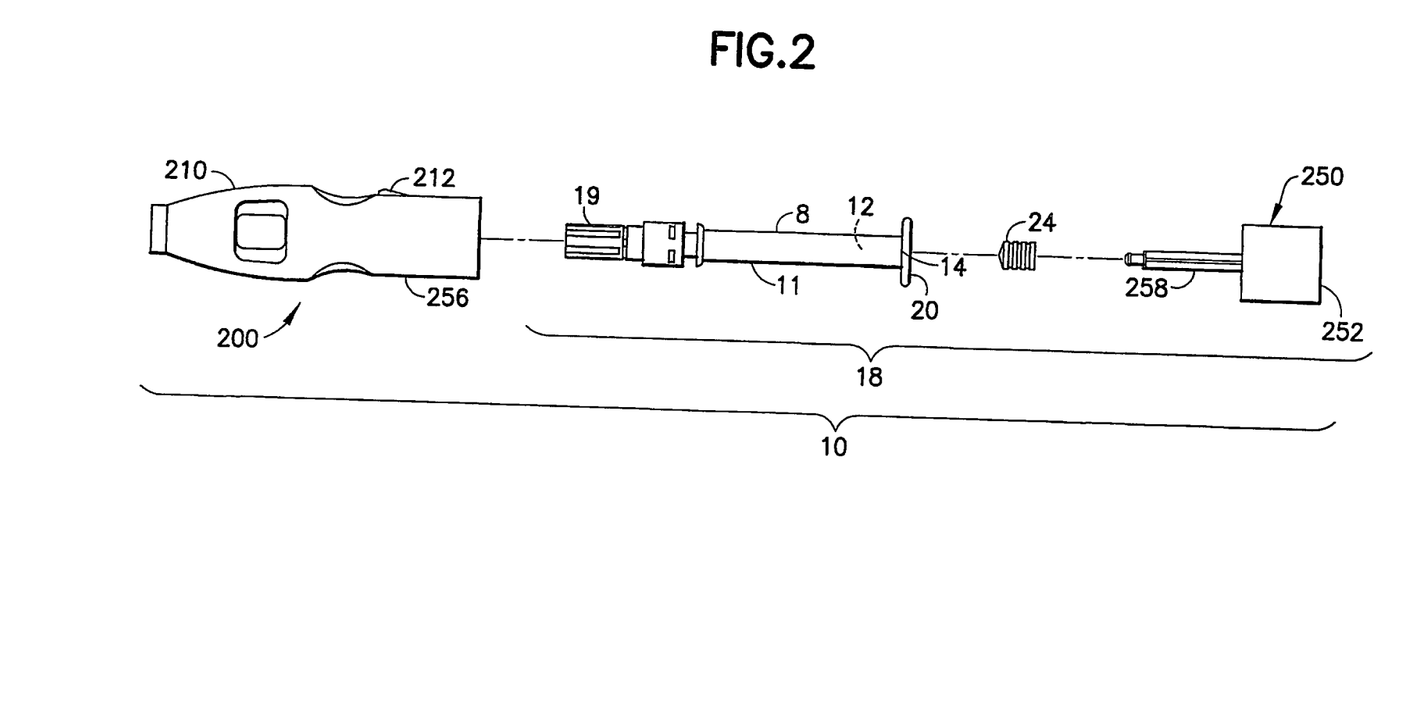
FIG. 2 is an exploded side view of the drug delivery device and holder of FIG. 1.
Figure 3:
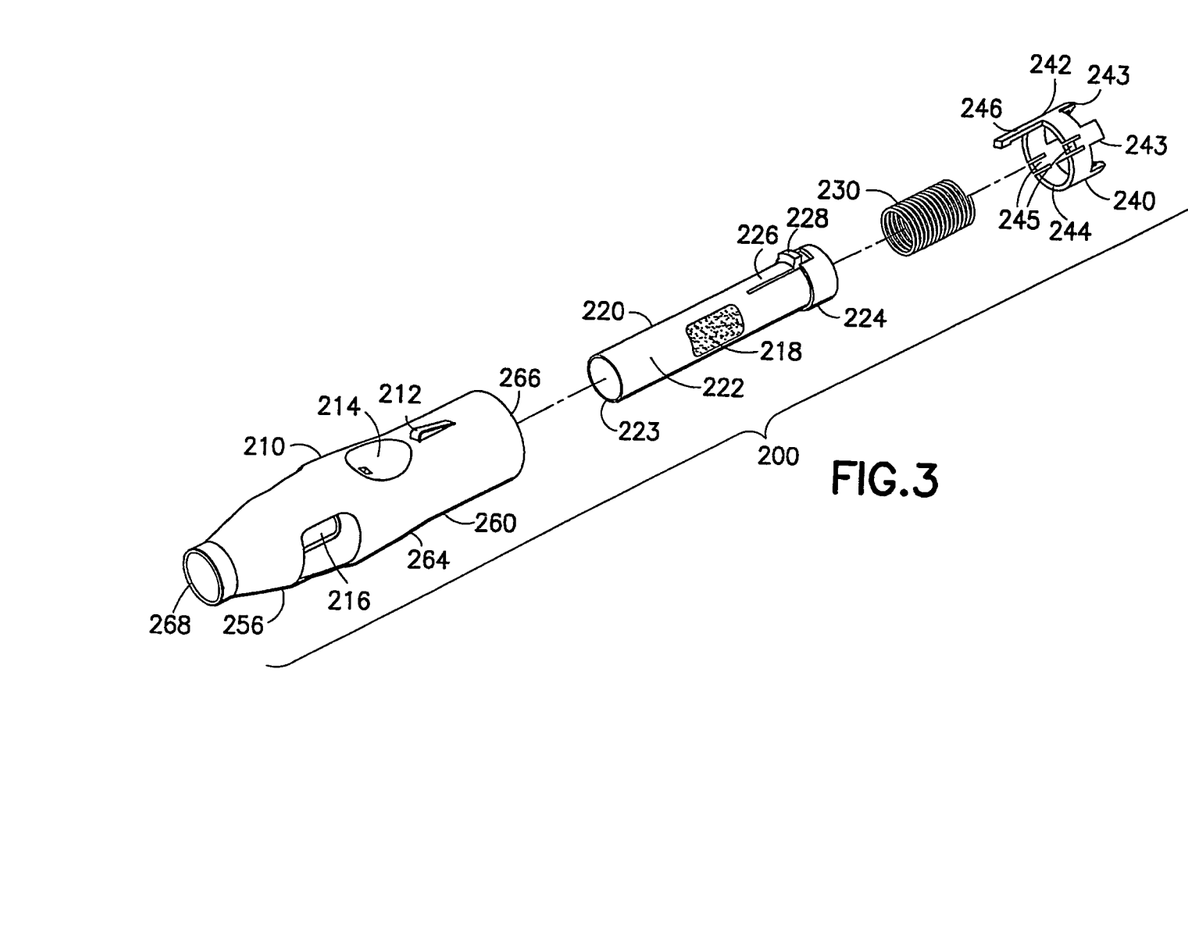
FIG. 3 an exploded perspective view of the holder of FIG. 1.

As best shown in FIG. 3, the holder 200 includes a housing 210, a safety shield 220, a biasing means 230, and a retainer ring 240. The syringe 18 is placeable within the syringe holder 200 and may be prefilled with the drug substance.

With reference to FIGS. 3-6, the housing 210 includes a housing body 260 which is cylindrical and has a longitudinal housing cavity 262. One or more windows 216 may extend through the wall of the housing body 260 to expose the housing cavity 262.

The housing body 260 has an outer surface which is preferably shaped to accommodate the thumb and middle finger of the user's hand to facilitate gripping of the housing 210, which may be by a single hand of the user. Such shaping of the outer surface of the housing body 260 may be by one or more depressions 214 which are preferably provided as a pair of diametrically opposed depressions 214 located on opposite sides of the housing body 260 to facilitate gripping of the syringe holder 200 during use (see, e.g., FIGS. 4 to 6). The depressions 214 may be textured or otherwise contain a feature that enhances gripping by the user. Alternative shapes of the outer surface of the housing body 260 to facilitate gripping are possible. For example, the intermediate portion 264 of the outer surface between the proximal and distal ends 266, 268 of the housing 210 may have a peripheral dimension which is reduced relative to the peripheral dimensions of the proximal and distal ends 266, 268 of the housing 210. Such a reduced peripheral dimension may provide the outer surface of the housing body 260 with the shape of an hourglass or venturi to accommodate the thumb and middle finger of the user's hand allowing a user's index finger to act on the pusher 250 as described below.

Preferably, the housing body 260 includes concentrically aligned inner and outer walls 261, 263 at the proximal end 266 thereof. An insertion gap 265, which is preferably generally annular, is defined between the walls 261, 263 and is sized to accommodate the cap wall 256. An inner wall slot 267 extends through the inner wall 261, distally from a proximal end 273 of the inner wall 261 and is formed to receive the ring lever described below. At the base of the inner wall slot 267, a housing edge 270 extends inwardly. A secondary slot 269, preferably having less depth than the inner wall slot 267, extends distantly from the housing edge 270 and terminates at a secondary edge 271. Preferably, the inner wall slot 267 and the secondary slot 269 are longitudinally aligned to form a continuous longitudinal slot.

The safety shield 220 includes a shield body 222 which is cylindrical and coaxially supported within the housing body 260. The proximal end of the shield body 222 terminates at a collar portion 224. The collar portion 224 is cylindrical and has increased inner and outer diameters relative to the adjoining portion of the shield body 222 resulting in an internal edge 225 which is annular and generally defines the distal end of the collar portion 224.

Figure 5:
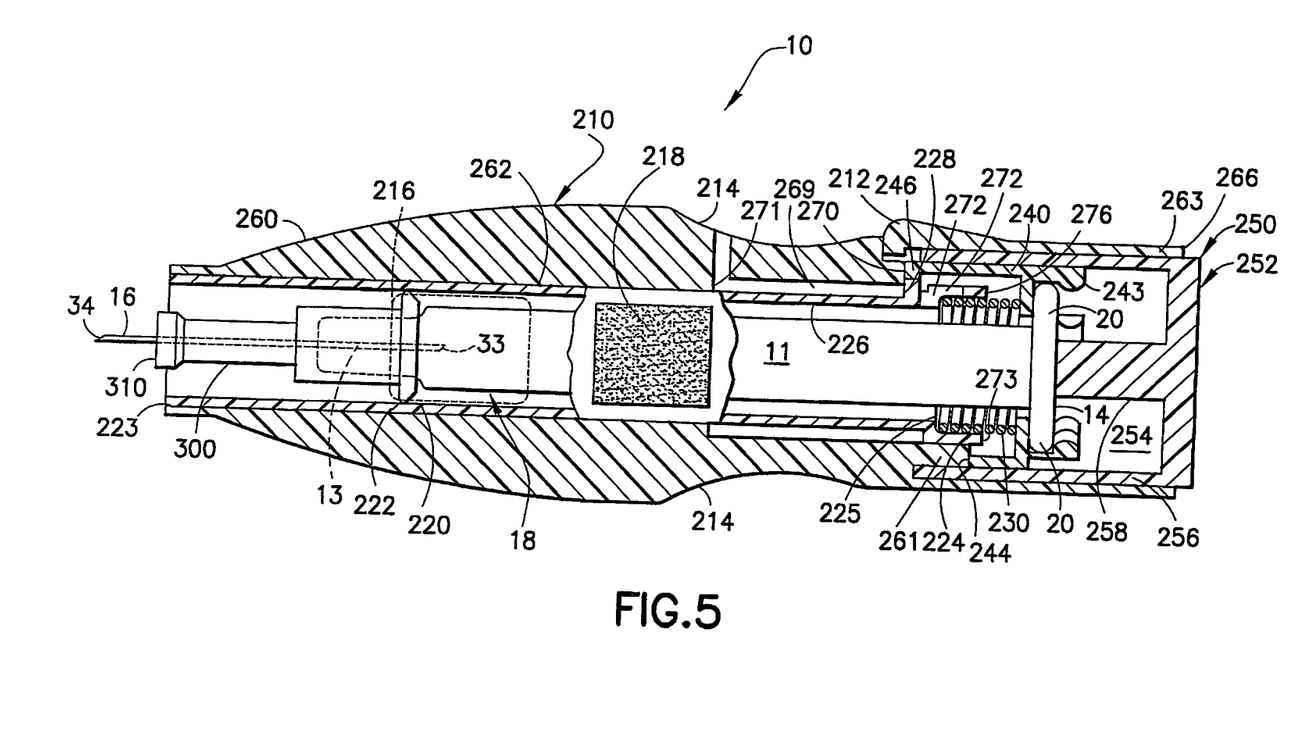
FIG. 5 is a cross-sectional side view of the holder and drug delivery device of FIG. 1 after use and prior to deployment of the safety shield.
Figure 6:
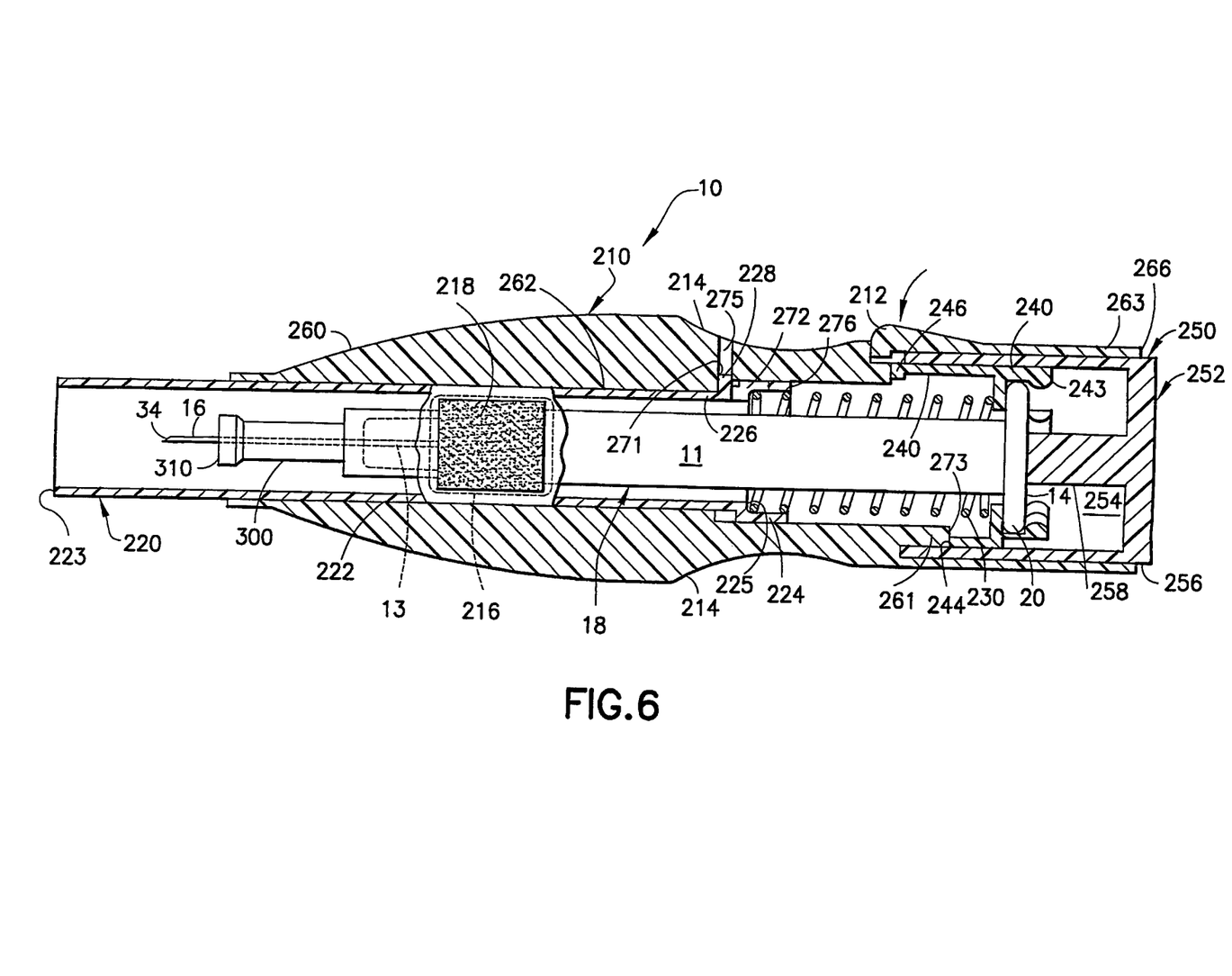
FIG. 6 is a cross-sectional side view of the holder and drug delivery device of FIG. 1 after deployment of the safety shield.
Figure 7:
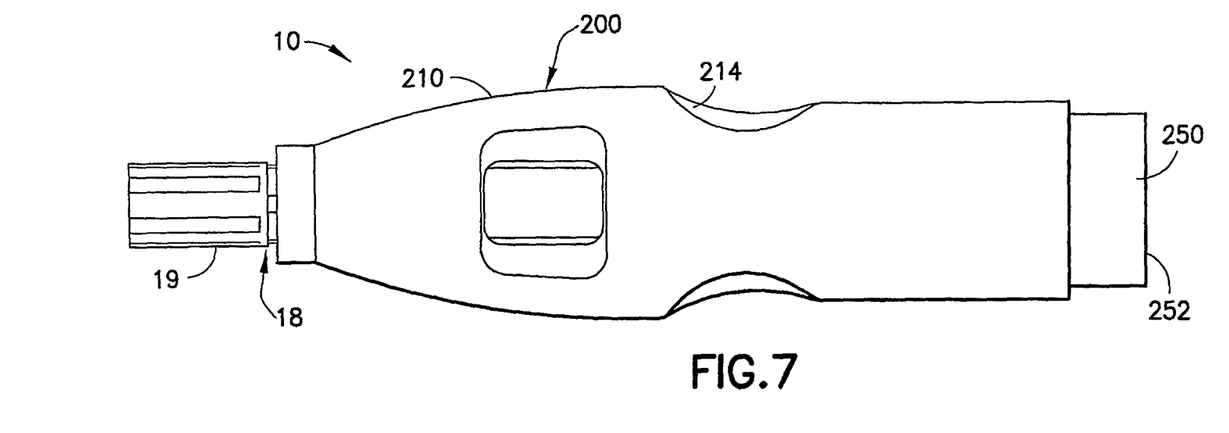
FIG. 7 is a side view of an alternative embodiment of the holder and drug delivery device of the present invention.

The safety shield 220 is longitudinally displaceable relative to the housing 210 between retracted and extended positions, as shown in FIGS. 5 and 6, respectively. When in the retracted position, the forward tip 34 of the needle cannula 16 is exposed and the injection device 10 may be used to inject a drug substance into the body of a patient. When in the extended position, the forward tip 34 of the needle cannula 16 is contained within the safety shield 220 and the safety shield 220 is preferably locked in place to prevent inadvertent and unintended contact with the forward tip 34 by a user or the patient. The safety shield 220 has a distal end 223 which is distal of the forward tip 34 when the safety shield 220 is in the extended position. Thus, the safety shield 220 prevents accidental needle-stick injury to the user or patient.

The safety shield 220 further includes a latch means which may be constituted by a shield latch 226 which is connected to the shield body 222 distally of the collar portion 224 and extends longitudinally relative thereto. The shield latch 226 terminates in a latch tab 228 which is adjacent to the collar portion 224 and extends radially outward. The shield latch 226, due to its cantilevered connection to the shield body 222, is able to be deflected radially between ready and released positions. The latch tab 228 is positioned to be within the inner wall slot 267 and engaged against the housing edge 270, with the shield 220 being in a retracted position. The engagement between the latch tab 228 and housing edge 270 resists longitudinal displacement of the safety shield 220 to the extended position, while the inner wall slot 267 prevents rotation of the safety shield 220 relative to the housing 260.

In addition, the safety shield 220 may include a marker or indicia 218, e.g., a red-colored tag. The indicia is located on the safety shield 220 such that it is not viewable through the window 216 with the safety shield 220 being in a retracted position (FIG. 4), but viewable through the window 216 with the safety shield 220 being in an extended position (FIG. 6). The indicia 218 provides a user with a warning that the injection device 10 has been used.

A plurality of components provided on the holder 200 and the syringe 18 comprise a release mechanism. The release mechanism may be in one of a ready position and a release position. When in the ready position, one of the components of the release mechanism is not in radial alignment with the other components of the release mechanism. When in the release position, all of the components of the release mechanism are radially aligned with each other, and the safety shield 220 may be released from its retracted position and biased towards its extended position. As discussed further, the release mechanism may automatically release the safety shield 220 from its retracted position at the end of an injection stroke. This embodiment is referred to herein as passive activation. Alternatively, one or more components of the release mechanism may require manipulation by the user to release the safety shield 220 from its retracted position. This embodiment is referred to herein as active activation.

In the embodiment of FIGS. 1-6, an active release mechanism is depicted. Specifically, the retainer ring 240 includes a ring body 242 which is coaxially supported around the syringe body 11 and longitudinally fixed thereto by a plurality of longitudinal ring clips 243, which may number five, extending proximally from the ring body 242, as shown in FIG. 3. Each of the ring clips 243 has a radially inward extending lip which, together with the ring body 242, sandwiches an annular proximal flange 20 which extends outwardly from the proximal end of the syringe body 11 (see, e.g., FIG. 4). The retainer ring 240 further includes longitudinal ring latches 245 connected to the ring body 242, preferably a pair in diametrically opposed relation to one another. The ring latches 245 are configured to engage the housing body 260 and, when so engaged, resist proximal longitudinal translation and rotational movement of the ring body 242 relative to the housing body 260.

The ring body 242 has an inner diameter which is larger than the outer diameter of the collar portion 224 of the safety shield 220 enabling the ring body 242 to overlap radially the collar portion 224 of the shield body 222, as shown in FIGS. 4 to 6. Preferably, distal edge 244 of the ring body 242 engages the proximal end 273 of the inner wall 261.

The retainer ring 240 includes a ring lever 246 which extends from the ring body 242 for radially inward deflection between ready and released positions. Upon assembly, the ring lever 246 is located in the inner wall slot 267 at generally the same longitudinal location as the latch tab 228. With the latch tab 228 being located in the inner wall slot 267 as indicated above, the ring lever 246 and the latch tab 228 are radially aligned and, as such, sufficient inward deflection of the ring lever 246 results in engagement of the ring lever 246 with the latch tab 228.

The biasing means may be constituted by a helical spring 230. The spring 230 is in coaxial relation to and external of the syringe body 11 between the retainer ring 240 and safety shield 220. The proximal end of the spring 230 is contained within the retainer ring 240, the inner diameter of which is larger than the outer diameter of the spring 230. The distal end of the spring 230 is contained within the collar portion 224 of the shield body 222, the inner diameter of which is also larger than the outer diameter of the spring 230.

In assembling the holder 200, the retainer ring 240 is secured to the housing body 260 by the ring clips 243, as described above. In an assembled state, as shown in FIG. 4, the spring is compressed resulting in the spring urging the safety shield 220 toward the extended position. This urging is resisted by the engagement between the latch tab 228 and the housing edge 270.

The holder 200 includes a means for deflection which, by way of non-limiting illustration in a first embodiment, is constituted by a pushbutton 212 formed in the outer wall 263 of the housing body 260 as shown in FIGS. 1 to 6. With the holder 200 assembled, the pushbutton 212, ring lever 246, and shield latch 224 are radially aligned on the housing body 260. The pushbutton 212 is positioned radially outward of the ring lever 246.

The pushbutton 212 may be selectively deflected radially inward into the insertion gap 265 by a user from ready to released positions. The pushbutton 212, ring lever 246 and shield latch 224 are sized to provide a gap or radial clearance between the pushbutton 212 and ring lever 246, and/or the ring lever 246 and shield latch 224. This radial clearance is sufficient such that, prior to the insertion of a portion of the drug delivery device into the radial clearance, the deflection of the pushbutton 212 to the released position does not result in disengagement of the shield latch 224 from the housing edge 270. For example, the elements herein are preferably configured so that insertion of the cap wall 256 into the insertion gap 265 prior to the end of an injection stroke, the deflection of the pushbutton 212 to the released position does not result in disengagement of the shield latch 224 from the housing edge 270. Preferably, the radial clearance is selected such that full deflection of a particular element, e.g., the pushbutton 212, shall not result in engagement with another of the elements of the release means, e.g., the ring lever 246. Additionally, it is preferred, although not necessary, a portion of the drug delivery device will not be inserted into the radial clearance until the injection is complete. Thus, the safety shield 220 will not move from the retracted position to the extended position before and until administration of an injection is complete and the stopper 24 has been moved longitudinally through the reservoir 12 so as to cause the entire contents thereof to be expelled through the needle cannula 16, i.e., at the end of an injection stroke. The injection stroke will generally coincide with the stopper 24 traversing the full length of the reservoir 12.

It should be understood by a person skilled in the art from the disclosure provided herein that the precise position of the stopper 24 does not necessarily determine completion of an injection stroke nor the point at which the safety shield 220 may be released from the retracted position and caused to move toward the extended position. Rather, radial alignment of all components of the release means determine the point at which the safety shield 220 may be released from its retracted position.

When the holder 200 is fully assembled as shown in FIG. 4 and the reservoir 12 contains fluid for injection into a patient, the inventive injection device 10 is ready for application to the patient. The holder 200 may be separately prepared from the syringe 18. The syringe 18 is insertable into the housing cavity 262 with the flange 20 being locked onto by the ring clips 243. Under certain (and appropriate) circumstances, the holder 200 may be disengaged from a used syringe 18 and re-used.

Initially, the housing body 260 is gripped by placing the thumb and middle finger against the portion of the outer surface of the housing body 260 which is shaped to accommodate the thumb and middle finger. This portion of the outer surface may be the depressions 214 such that the end of the thumb is inserted into one of the depressions 214 and the end of the middle finger is inserted into the other of the depressions 214. Alternatively, the portion of the outer surface against which the thumb and middle finger is placed may be the intermediate portion 264 of the housing body 260 having the shape of an hourglass or a venturi where the intermediate portion 264 has a reduced peripheral dimension relative to the proximal and distal ends 266, 268 of the housing 210.

With the housing body 260 being gripped, the housing 210 is oriented relative to the skin of the patient such that the injection device 10 is generally perpendicular to the skin of the patient and the forward tip 34 of the needle cannula 16 is adjacent to the skin of the patient. The holder 200 is then displaced toward the skin in generally perpendicular relation thereto such that the forward tip 34 punctures the skin and enters the patient's body.

The index finger of the user's hand is then moved into contact with the pusher cap 252, and the pusher cap 252 is depressed to advance the pusher stem 258 into the reservoir 12. The advancement of the pusher stem 258 into the reservoir 12 results in movement of the stopper 24 in a proximal to distal direction and fluid injection through the needle cannula 16. The pusher stem 258 is advanced a distance sufficient to cause the stopper 24 to traverse the longitudinal length of the reservoir 12, this advancement defining the injection stroke. At the end of the injection stroke, the cap wall 256 is inserted into the insertion gap 265 between the pushbutton 212 and ring lever 246, as shown in FIG. 5. Preferably, the cap wall 256 has sufficient longitudinal length to be interposed between the pushbutton 212 and the ring lever 246. Consequently, the radial clearance between the pushbutton 212 and the ring lever 246 is eliminated. Prior to the injection stroke, it is preferred that the cap wall 256 be located proximally of the ring lever 246.

To activate the safety shield 220, the pushbutton 212 is inwardly deflected resulting in inward deflection of the cap wall 256 of the pusher cap 252 and, in turn, resulting in the deflection of the ring lever 246 to the released position thereof. This causes the deflection of the shield latch 224 to the released position thereof resulting in the latch tab 228 disengaging from the housing edge 270. This enables the spring 230 to urge the safety shield 220 to the extended position, with the latch tab 228 traveling through the secondary slot 269, to cover the forward tip 34 of the needle cannula 16 upon completion of an injection, as shown in FIG. 6. The latch tab 228 engages the secondary edge 271 to prevent further distal movement of the safety shield under force of the spring 230. Preferably, a locking slot 275 extends radially from the secondary edge 271 formed to entrap the latch tab 228. In this manner, the safety shield 220 may be locked in the extended position. The secondary slot 269 and/or the locking slot 275 prevents rotation of the safety shield 220 relative to the housing 260 with the safety shield 220 being in the extended position.

Activation of the safety shield 220 is thus only possible at the end of the injection stroke, when the pusher 250 is fully engaged into the housing body 260. Depression of the pushbutton 212 prior to an injection or after partial injection of the fluid contents has no effect, i.e., the safety shield 220 can only be released and caused by the spring 230 to move to cover the needle at the end of the injection stroke when the cap wall 256 is fully engaged in the insertion gap 265. The pushbutton 212, cap wall 256, and ring lever 246 establish components of a release mechanism based on the cooperation thereof, when radially aligned, to deflect the shield latch 224 to the released position thereof Although not shown, in addition or in the alternative, the push cap 252 may include a wall or other element configured to fill a radial clearance between the ring lever 246 and the latch tab 228. Also, the shield latch 224 may be configured to be directly deflected by the cap wall 256, without the intervening ring lever 246.

Figure 8:
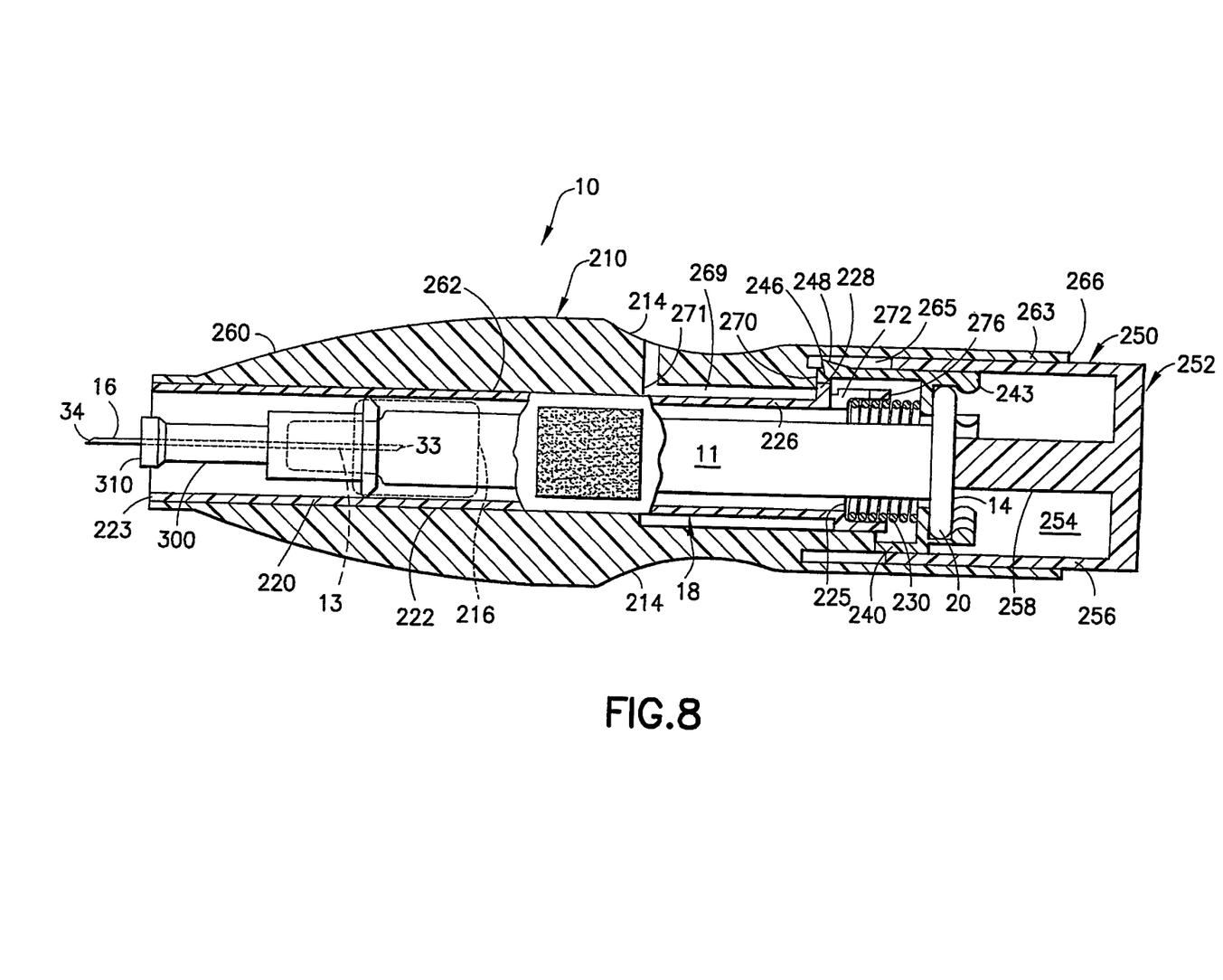
FIG. 8 is a cross-sectional side view of the holder and drug delivery device of FIG. 7 prior to use.

In a second embodiment of the holder 200, which is depicted in FIGS. 7 to 10, deployment of the safety shield 220 occurs automatically at the end of the injection stroke and when the cap wall 256 is fully engaged in the housing body 210. No external pushbutton 212, or equivalent, is required. Rather, in this second embodiment, the means for inward deflection includes a molded in ramp 248 on a surface of the retainer ring 240, as shown in FIG. 8. This results in activation of the safety shield 210 at the end of the injection stroke without an additional action by the user, e.g., depression of a pushbutton or other activating means.

With the injection device 10 assembled, the ramp 248, ring lever 246, and shield latch 224 have generally the same longitudinal position relative to the housing body 260 enabling the radial alignment therebetween. The ramp 248 protrudes radially outward from the ring lever 246 such that a proximal portion of the ramp 248 has a smaller radial dimension relative to a radial dimension of a distal portion of the ramp 248.

Figures 9, 10:
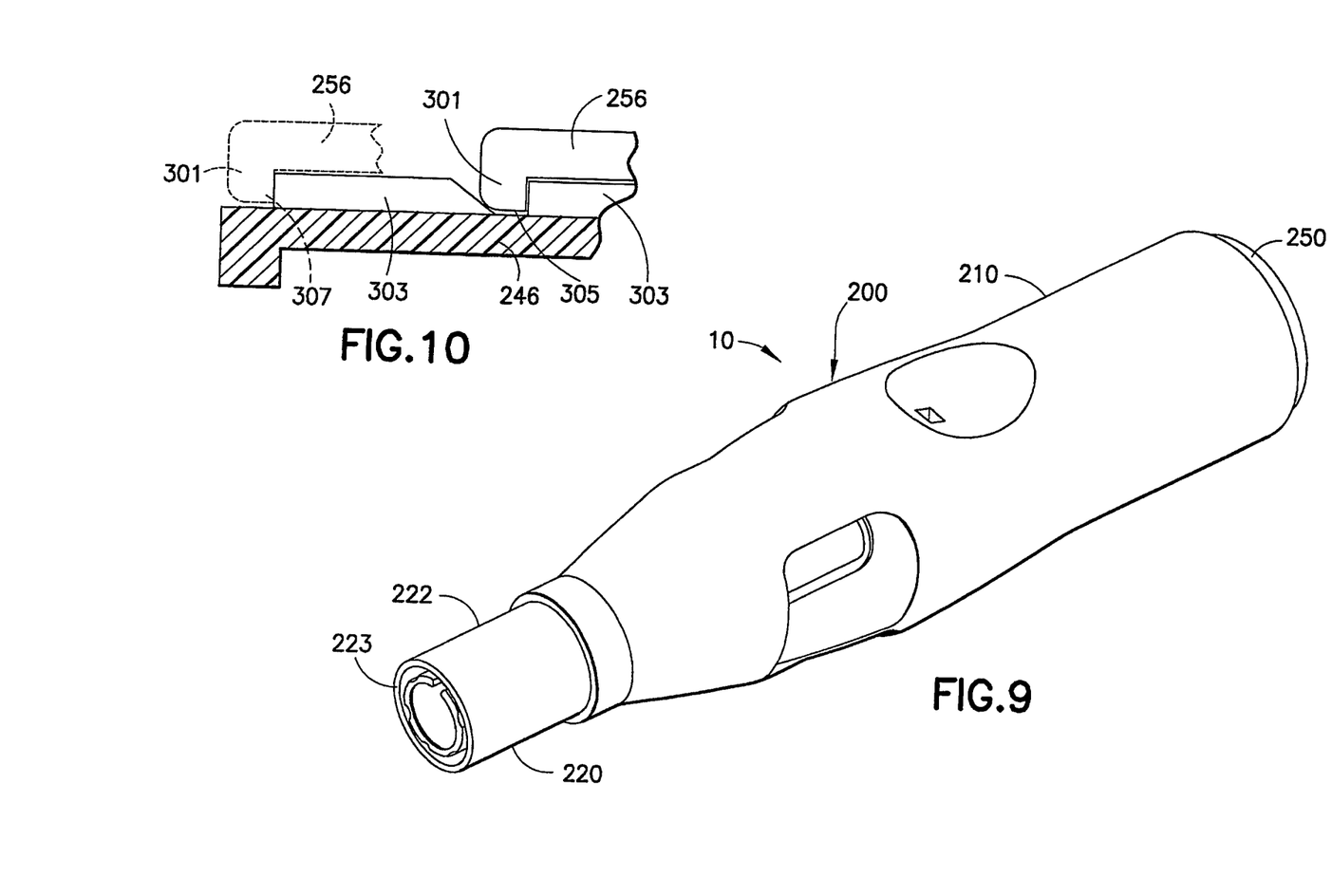
FIG. 9 is a perspective view of the holder and drug delivery device of FIG. 7 after use and after deployment of the safety shield.
FIG. 10 is a schematic of a pusher cap locking mechanism useable with the subject invention.

Longitudinal insertion of the cap wall 256, upon completion of the injection stroke, between the housing body 260 and ramp 248 causes the deflection of the ring lever 246 to the released position thereof This, in turn, causes the deflection of the shield latch 224 to the released position thereof resulting in the deployment of the safety shield 220, as shown in FIG. 9 and in the same manner described herein for the syringe holder 200 including the pushbutton 212. Accordingly, the ramp 248 provides for automatic deployment of the safety shield 220 upon completion of an injection stroke and insertion of the cap wall 256 between the housing body 260 and ramp. The cap wall 256, ramp 248, and ring lever 246 establish components of the release mechanism based on the cooperation thereof, when radially aligned, to deflect the shield latch 224 to the released position thereof.

Advantageously, the insertion gap 265 is adjacent to the ramp 248, and with no pushbutton 212, the outer wall 263 is formed solidly and continuously about the ramp 248. Accordingly, no direct external access to the ramp 248 is provided. Also, the insertion gap 265 ensures that no element of the holder 200 is adjacent to the ramp 248. In this manner, unwanted deflection of the ring lever 246 is avoided which may result in inadvertent activation of the safety shield 220.

As an additional aspect of the injection device 10, and with reference to FIG. 10, a detent 301 may be provided on the cap wall 256, preferably at the bottom edge thereof. A longitudinal protrusion 303 may also extend from the ring lever 246 having a notch 305 into which the detent 301 may be seated to restrain movement of the pusher cap 252. With sufficient distal force, the detent 301 may be unseated, allowing the push cap 252 to advance distally during an injection stroke. The longitudinal protrusion 303 may be provided with a shaped end or secondary notch 307 into which the detent 301 may be seated upon completion of the injection stroke to restrain movement of the pusher cap 252. As will be appreciated by those skilled in the art, the detent 301 and notches 305, 307 may be formed to prevent proximal movement of the pusher cap 252 relative to the ring lever 246.

Further, the syringe 18 may be provided with a removable tip cap 19, as depicted in FIGS. 1, 2, 7 and 8, which covers the forward or distal tip 34 of the needle cannula 16 prior to use for safety and sterility and/or after use as an additional safety device.

While the invention has been described by reference to certain preferred embodiments, it should be understood that numerous changes could be made within the spirit and scope of the inventive concept described. Accordingly, it is intended that the invention not be limited to the disclosed embodiments, but that it have the full scope permitted by the language of the following claims.

What is claimed is:
1. An injection device comprising:
a drug delivery device comprising:
a body having a reservoir for containing a fluid, said body having a distal port through which the fluid may exit, said body further having a proximal port; a pusher including a pusher cap having a cap wall,
a pusher stem connected in coaxial relation to said pusher cap and a stopper provided at an end of said pusher stem, said stopper being movable in said reservoir in a proximal to distal direction over a length defining an injection stroke, wherein said cap wall extends coextensively, in a spaced relationship, about a portion of said pusher stem;
a needle cannula provided on said body in fluid communication with said reservoir; and
a holder comprising:
a housing having a longitudinal housing cavity;
a safety shield coaxially supported in said housing cavity, said safety shield being longitudinally displaceable relative to said housing from a retracted position, in which said forward tip of said needle cannula is exposed, to an extended position, in which said forward tip of said needle cannula is contained within said safety shield, said safety shield further comprising a shield latch deflectable between ready and released positions, said shield latch engaging said housing when said shield latch is in said ready position to hold said safety shield in said retracted position;
a retainer ring comprising a ring body which is coaxially supported around said body, said retainer ring further comprising a ring lever connected to said ring body for radially inward deflection between ready and released positions;
a spring supported within said housing and coupled to said safety shield to urge said safety shield toward said extended position; and
a means for deflection connected to said housing; said cap wall being insertable between said deflection means and ring lever, said deflection means providing for inward radial deflection of said cap wall resulting in said deflection of said ring lever to said released position thereof causing said deflection of said shield latch to said released position thereof resulting in said shield latch disengaging from said housing and movement of said safety shield toward said extended position,
wherein said deflection means comprises a pushbutton connected to said housing for inward radial deflection from ready to released positions, said pushbutton, said ring lever and said shield latch being positioned and sized to provide a sufficient radial clearance such that, prior to insertion of said cap wall between said pushbutton and said ring lever, said deflection of said pushbutton to said released position does not cause disengagement of said shield latch from said housing, wherein insertion of said cap wall between said pushbutton and said ring lever allowing for said pushbutton, said ring lever and said shield latch to be deflected to said respective ready positions thereof with said deflection of said pushbutton to said released position of said pushbutton causing inward radial deflection of said cap wall resulting in said deflection of said ring lever to said released position thereof causing said deflection of said shield latch to said released position thereof resulting in said shield latch disengaging from said housing and movement of said safety shield toward said extended position.

2. An injection device according to claim 1, wherein said cap wall is cylindrical.

3. An injection device according to claim 1, wherein a maximum extent of said insertion of said stopper into said reservoir defines an end of said injection stroke, said pusher stem having a sufficient length and said pusher cap being longitudinally positioned thereon such that said cap wall is inserted between said deflection means and ring lever upon said end of said injection stroke.

4. An injection device according to claim 1, wherein said housing having a longitudinal slot for radially aligning said ring lever and shield latch relative to said deflection means, a housing edge extending into said slot engaged by said shield latch when said shield latch is in said ready position for holding of said safety shield in said retracted position.

5. An injection device according to claim 1, wherein said safety shield comprises a cylindrical shield body.

6. An injection device according to claim 1, wherein said ring body is coupled to said body such that said ring body is adjacent to a proximal end of said safety shield when said safety shield is in said retracted position.

7. An injection device according to claim 1, wherein said retainer ring is coupled to said body, said spring being helical and in coaxial relation to said syringe body, said spring being external of said body and longitudinally positioned between said retainer ring and said safety shield with compression of said spring providing said urging by said spring of said safety shield to said extended position.

8. An injection device according to claim 1, wherein said deflection of said shield latch to said released position thereof is radially inward.

9. An injection device according to claim 1, wherein said drug delivery device comprises a limiter at a distal end of said body, said limiter defining a skin engaging surface, said forward tip of said needle cannula extending beyond said skin engaging surface a distance ranging from 0.5 mm to 3 mm.

10. A combination of a drug delivery device and a holder for the drug delivery device, said combination comprising:
a drug delivery device comprising:
a body having a reservoir for containing a fluid, said body having a proximal port and a distal port through which the fluid may exit;
a retainer ring comprising a ring body which is coaxially supported around said body, said retainer ring further comprising a ring lever connected to said ring body for radially inward deflection between ready and released positions;
a pusher including a pusher cap having a cap wall, a pusher stem connected in coaxial relation to said pusher cap, and a stopper provided at an end of said pusher stem, said stopper being movable in said reservoir in a proximal to distal direction over a length defining an injection stroke; and
a needle cannula secured to said body in fluid communication with said reservoir,
a holder comprising:
a housing defining a longitudinal housing cavity for accommodating the drug delivery device;
a safety shield coaxially supported in said housing cavity, said safety shield being longitudinally displaceable relative to said housing in a proximal to distal direction from a retracted position to an extended position;
latch means deflectable between ready and released positions, said latch means engaging said housing when said latch means is in said ready position to hold said shield in said retracted position;
biasing means for biasing said safety shield toward said extended position; and
deflection means radially aligned with, and positioned radially outwardly of, said latch means, a gap being defined between said deflection means and said latch means, said gap being formed to receive a portion of the drug delivery device, wherein, with said gap being open, deflection of said deflection means does not cause disengagement of said latch means from said housing, and, wherein, with a portion of the drug delivery device being received in the gap and interposed between said deflection means and said latch means, deflection of said deflection means results in deflection of said latch means to said released position thereof with said latch means disengaging from said housing and movement of said safety shield toward said extended position,
wherein said deflection means comprises a pushbutton connected to said housing for inward radial deflection from ready to released positions, wherein insertion of said cap wall between said pushbutton and said ring lever allows for said pushbutton, said ring lever and said latch means to be deflected to said respective ready positions thereof with said deflection of said pushbutton to said released position of said pushbutton causing inward radial deflection of said cap wall resulting in said deflection of said ring lever to said released position thereof causing said deflection of said latch means to said released position thereof resulting in said latch means disengaging from said housing and movement of said safety shield toward said extended position.

11. A combination according to claim 10, wherein said deflection means requires manual activation by a user.

12. A combination according to claim 10, wherein said gap is defined between said pushbutton and said ring lever.

13. A combination according to claim 10, wherein said ring lever is radially aligned with said pushbutton.

14. A combination according to claim 10, wherein said drug delivery device further comprises a limiter at a distal end of said body, said limiter defining a skin engaging surface, said forward tip of said needle cannula extending beyond said skin engaging surface a distance ranging from 0.5 mm to 3 mm.

15. A combination according to claim 10, wherein said biasing means comprises a spring supported within said housing and positioned to urge said safety shield toward said extended position.

16. A combination according to claim 10, wherein said latch means comprises a shield latch deflectable between said ready and released positions, said shield latch engaging said housing when said shield latch is in said ready position to hold said safety shield in said retracted position.

* * * * *